US006841174B2

(12) United States Patent
Shalaby et al.

(10) Patent No.: US 6,841,174 B2
(45) Date of Patent: Jan. 11, 2005

(54) HERBAL COMPOSITIONS AND TREATMENT METHODS

(75) Inventors: Said I. A. Shalaby, Cairo (EG); Essam M. A. Hob Allah, Cairo (EG)

(73) Assignee: Zeyad Technologies LLC, Yonkers, NY (US)

(*) Notice: Subject to any disclaimer, the term of this patent is extended or adjusted under 35 U.S.C. 154(b) by 0 days.

(21) Appl. No.: 09/955,877

(22) Filed: Sep. 19, 2001

(65) Prior Publication Data

US 2002/0160065 A1 Oct. 31, 2002

Related U.S. Application Data

(60) Provisional application No. 60/233,856, filed on Sep. 20, 2000.

(51) Int. Cl.$^7$ ................................................ A61K 35/78
(52) U.S. Cl. ...................... 424/725; 424/773; 424/774; 424/775; 424/776; 424/777; 424/779
(58) Field of Search .............................. 424/195.1, 725, 424/773, 774, 776, 777, 779; 514/783

(56) References Cited

U.S. PATENT DOCUMENTS

| 5,648,089 A | * | 7/1997 | Sawkat ....................... 424/434 |
| 5,874,804 A | | 2/1999 | Rogers |
| 5,876,728 A | | 3/1999 | Kass et al. |

FOREIGN PATENT DOCUMENTS

EP            793964       9/1999

OTHER PUBLICATIONS

Revilla et al. Comparison of Several Procedures Used for the Extraction of Anthocyanins from Red Grapes; J. Agric. Food Chem, 1998, 46, 4592–4597.*
Mylonakis et al. Plasma Viral Load Testing in the Management of HIV Infection; American Family Physician; Feb. 2001, pp. 1–7.*
HIV/AIDS Monitoring; Improved Viral Load Test Approved by FDA; Blood Weekly; Atlanta; Sep. 2002 pp. 1–2.*
Animal Models (HBV0; Trimera Disease Model Developed for Hepatitis B; Cancerweekly Plus; Atlanta; 2/199 pp. 1–2.*
Davis, G. Treatment of Chronic Hepatitis C; British Medical Journal; Nov. 2001 pp. 1–3.*
Harvard School of Public Health Jan. 2004, <http://www.researchmatters.harvard.edu/story.php?article_id=673>.
Buckwold, Beer, Donis, 2003 "Bovine viral diarrhea as a surrogate model of hepatitis C virus for the evaluation of anti–viral agents" Antiviral Research vol. 60(1):1–15;
Cost of Developing a New Drug Increases to About $1.7 Billion By Peter Landers, Wall Street Journal Dec. 8, 2003 <http://online.wsj.com/article/0,,SB107083909136415400–email,00.html>.
Abramowicz M, ed., "Enfuviritide (Fuzeon) for HIV Infection" Med Lett Drugs Ther. 2003 Jun. 23; 45(1159): 49–50.

El–Awady, et al., Clinica Chimica Acta, 283(1–2);1–14 (1999).
McHutchison et al., "Interferon Alpha–2b Alone or in Combination with Ribavirin as Initial Treatment fro Chronic Hepatitis C", New England Journal of Medicine vol. 339 No. 21 Nov. 19, 1998, 1485–1492;
Yokozawa, et al., J. Traditional Medicine, 15(1):45–51 (1998).
Alter, M.J., Hepatology, 26(1):62S–65S (1997).
Alam, et al., Phytotherapy Research, 10(1):58–61 (1996).
D.S. Chen; J. Formos. Med. Assoc., 95(1):6–12 (1996).
Detre, et al., Viral Hepatitis Rev., 2:219–228 (1996).
D.C. Dale and D.D. Federman, eds., Sci. Amer. Medicine, New York, 4(8):1–10 (1996).
Hibbs, et al., J. Infect. Dis. 168:789–790 (1993).
Lok, et al., Gastroenterology, 105(6):1833–1838 (1993).
Flint SJ et al., Principles of Virology: Molecular Biology, Pathogenesis, and Control, ASM Press, Washington DC, 1990, p. 691.
Medicinal Plants of North Africa, Loutfy Boulos, Reference Publications, Inc., pp. 150–51 (1983).
Medicinal Plants of North Africa, pp. 74–75, 92–93 (1983).
Bergmeyer and Horder, Clinica Chemica Acta 105:147f–154f (1980).
Encyclopedia of Common Natural Ingredients, Used in Food, Drugs, and Cosmetics, John Wiley & Sons, New York, p. 169 (1980).
International Federation of Clinical Chemistry, Scientific Committee, J. Clin. Chem. Clin. Biochem., 18521–534 (1980).
Bergmeyer H. U. Methods of Enzymatic Analysis. Verlag Chemic, (1978), pp. 130–135.
Babbar, et al.,Ind. J. Exp. Biol., 8:304–312 (1970).
Linus Pauling, General Chemistry, New York, Dover Publications, Inc., 1970, p. 744.

* cited by examiner

*Primary Examiner*—Patricia Patten
(74) *Attorney, Agent, or Firm*—Baker Botts L.L.P.

(57) ABSTRACT

The invention provides herbal compositions with antiviral properties comprising extracts of *Foeniculum vulgare, Nigella sativa, Centaurium erythrae* (spicatum or pulchellum), *Cynara cardunculus* var *scolymus, Inula helenium* (viscosa), *Solenostema argel, Sesbania aegyptiaca* (sesban), *Cichorium intybus* (pumilum), *Cymbopogon proximus, Hemidesmus indicus, Rheum officinale, Cuminum cyminum*, and combinations thereof. The invention further provides herbal compositions with antiviral properties comprising an extract from the leaves or seed of *Sesbania aegyptiaca* (sesban) and at least one additional herbal extract selected from the group consisting of seed of *Nigella sativa*, shoot of *Cichorium intybus* (pumilum), whole plant of *Cymbopogon proximus*, rhizome of *Hemidesmus indicus*, leaves of *Solenostema argel*, rhizome of *Rheum officinale*, and fruit of *Ecballium elaterium*. The present invention also provides methods for treating a subject with a viral infection, particularly infections with hepatitis B virus or hepatitis C virus. The methods comprise administering to a subject an effective amount of a herbal composition selected from among the herbal compositions of the invention.

3 Claims, No Drawings

HERBAL COMPOSITIONS AND TREATMENT METHODS

This application is based on U.S. Provisional Application No. 60/233,856, filed Sep. 20, 2000, which is incorporated herein in its entirety by reference.

BACKGROUND OF INVENTION

Hepatitis is a disease of the liver, which is usually caused by viral infections. A significant number of patients suffering from hepatitis are infected with either hepatitis B virus (HBV) or hepatitis C virus (HCV). HCV is an RNA virus with a virion size of 30–60 nm. HBV is a DNA virus with a virion size of 42 nm (D. S. Chen, J. Formos. Med. Assoc., 95(1):6–12 (1996)). Serious complications of hepatitis can include cirrhosis, hepatic failure, liver cancer and death.

Nearly 4 million people in the United States and 100 million worldwide are infected with the hepatitis C virus (Alter, M. J., Hepatology, 26(1):625–655 (1997)). In fact, chronic hepatitis C is the most common cause of chronic liver disease and is the leading indication for liver transplantation in the United States (Detre, et al., Viral Hepatitis Rev., 2:219–228 (1996)).

Egypt, where 14–24% of blood donors are anti-HCV positive, has the highest HCV donor infection rates (Hipps, et al., Infect. Dis. 168:789–790 (1993)).

Hepatitis B is a major health problem worldwide, particularly in Asia and Africa. Approximately 300 million people are chronically infected with HBV worldwide and more than one million carriers of HBV are found in the United States. HBV carriers not only become long-term reservoirs of the virus, but also may develop chronic liver disease and have a greatly increased risk of developing liver cirrhosis and cancer.

Unfortunately, there are few effective treatments for hepatitis. Treatment of HCV with recombinant-alpha interferon has a limited long term efficacy with a response rate of only about 25% (D. S. Chen, J. Formos. Med. Assoc., 95(1):6–12 (1996)). A long-term relapse rate of 24% was reported in Chinese patients with chronic hepatitis B who underwent interferon therapy (Lok, et al., Gastroenterology, 105(6):1833–1838 (1993)). Furthermore, interferon is associated with a number of adverse side effects, including thrombocytopenia, leucopenia, bacterial infections, and influenza like symptoms. Other agents used in the treatment of hepatitis include the nucleoside analog ribavirin and ursodeoxycholic acid. However, neither interferon nor ribavirin have been shown to be particularly effective (D. C. Dale and D. D. Federman, eds. Medicine Sc. Amer., Inc., New York, 4(8):1–8 (1995)).

The use of herbal therapy and folk medicines has been known for thousands of years in China. In fact, records on the use of herbs date back to Biblical times. However, only recently have scientists begun exploring the possible role for herbs in treatment of viral infections. For example, extracts of *Hemidesmus indicus* rhizomes (Family: Asclepiadaceae) have been found to have anti-viral activity against DNA and RNA viruses (Babbar, et al., Ind. J Exp. Biol., 8:304–312 (1970)). Likewise, extracts from the root of the *Ecballium elaterium* have been used to treat HCV and HBV (EP 0793964 and U.S. Pat. No. 5,648,089). While research in the field of herbal medicines has increased, much remains to be learned about the effectiveness of such herbal remedies.

In view of the above, there is a continuing need in the art for alternative options for treating viral infections such as HCV and HBV. Moreover, there is a need in the art for treatment options that provide minimal side effects.

Accordingly, it is an object of the present invention to provide herbal compositions and methods for treating viral infections such as HCV and HBV. Moreover, it is object of the present invention to provide compositions and methods for treatment that provide minimal side effects to the subject.

SUMMARY OF THE INVENTION

The present invention provides herbal compositions having anti-viral properties and methods of treating viral infections. In one embodiment, the present invention provides a primary herbal composition which comprises:

(a) an extract from the leaves or seed of *Sesbania aegyptiaca* (sesban); and (b) at least one additional herbal extract selected from the group consisting of seed of *Nigella sativa*, shoot of *Cichorium intybus* (pumilum), whole plant of *Cymbopogon proximus*, rhizome of *Hemidesmus indicus*, leaves of *Solenostema argel*, rhizome of *Rheum officinale*, and fruit of *Ecballium elaterium*.

In another embodiment, the herbal composition does not contain *Ecballium elaterium* and includes two additional herbal extracts other than *Ecballium elaterium*. The herbal composition can also include at least one auxiliary herbal extract selected from the group consisting of seed of *Foeniculum vulgare*, shoot of *Centaurium erythrae* (spicatum or pulchellum), flowers, leaves or stem of *Cynara cardunculus* var scolymus, root of *Inula helenium* (viscosa) and seed of *Cuminum cyminum*. The herbal compositions can further include a physiologically-acceptable carrier.

In accordance with the invention, several particular embodiments of the primary herbal compositions are provided. In a first particular embodiment, a herbal composition is provided which comprises extracts from: (a) seed of *Foeniculum vulgare*; (b) seed of *Nigella sativa*; (c) shoot of *Centaurium erythrae* (spicatum or pulchellum); (d) flowers, leaves or stem of *Cynara cardunculus* var scolymus; (e) root of *Inula helenium* (viscosa); (f) leaves of *Solenostema argel*; (g) leaves or seed of *Sesbania aegyptiaca* (sesban); (h) shoot of *Cichorium intybus* (pumilum); (i) whole plant of *Cymbopogon proximus*; (j) rhizome of *Hemidesmus indicus*; (k) rhizome of *Rheum officinale*; and (l) seed of *Cuminum cyminum*.

In a second particular embodiment, a herbal composition is provided which comprises extracts from: root of *Inula helenium* (viscosa); shoot of *Centaurium erythrae* (spicatum or pulchellum); seed of *Nigella sativa*; leaves or seed of *Sesbania aegyptiaca* (sesban); and rhizome of *Hemidesmus indicus*.

In a third particular embodiment, a herbal composition is provided which comprises extracts from: rhizome of *Hemidesmus indicus*; flowers, leaves or stem of *Cynara cardunculus* var *scolymus*; shoot of *Centaurium erythrae* (spicatum or pulchellum); seed of *Foeniculum vulgare*; leaves of *Solenostema argel*; shoot of *Cichorium intybus*; and leaves or seed of *Sesbania aegyptiaca* (sesban).

In a fourth particular embodiment, a herbal composition is provided which comprises extracts from: seed of *Nigella sativa*; shoot of *Centaurium erythrae* (spicatum or pulchellum); leaves or seed of *Sesbania aegyptiaca* (sesban); seed of *Foeniculum vulgare*; and whole plant of *Cymbopogon proximus*.

In a fifth particular embodiment, a herbal composition is provided that comprises extracts from: rhizome of *Rheum officinale*; seed of *Cuminum cyminum*; root of *Inula helenium* (viscosa); flowers, leaves or stem of *Cynara cardunculus* var scolymus; seed of *Foeniculum vulgare*; and leaves or seed of *Sesbania aegyptiaca* (sesban).

TABLE 1

| Plant | Organs Used to Prepare Extracts Embodiments | | | | |
|---|---|---|---|---|---|
| | 1 | 2 | 3 | 4 | 5 |
| *Foeniculum vulgare* | Seed | | Seed | Seed | Seed |
| *Nigella sativa* | Seed | Seed | | Seed | |
| *Centaurium erythrae* | Shoot | Shoot | Shoot | Shoot | None |
| *Cynara cardunculus var scolymus* | Flowers, leaves or stem | | Flowers, leaves or stem | | Flowers, leaves or stem |
| *Inula helenium* | root | root | | | root |
| *Solenostema argel* | leaves | | leaves | | |
| *Sesbania aegyptiaca* | leaves or seed | leaves or seed | leaves or seed | leaves or seed | leaves or seed |
| *Cichorium intybus* | shoot | | shoot | | |
| *Cymbopogon proximus* | whole plant | | | whole plant | |
| *Hemidesmus indicus* | rhizome | | rhizome | | |
| *Rheum officinale* | rhizome | rhizome | | | rhizome |
| *Cuminum cyminum* | seed | | | | seed |

Gray boxes: no additives derived from indicated plant were added

The present invention also provides a method for treating a viral infection, which comprises administering to a subject an effective amount of a primary herbal composition being selected from among the herbal compositions of the invention. The herbal compositions preferably further comprise at least one of the auxiliary herbal extracts of the invention to ameliorate potential side effects and to facilitate treatment of the viral infection. In a more preferred embodiment, a secondary herbal composition is also administered to the subject which preferably comprises an extract of the fruit of *Ecballium elaterium*. The primary herbal composition is preferably in powder form and more preferably administered orally. The secondary herbal composition is preferably in liquid form and more preferably administered orally. The subjects to be treated are preferably subjects in need of treatment (suffering from a viral infection). Subjects to be treated are preferably mammals, particularly humans. Viral infections to be treated include hepatitis B, hepatitis C or a combination of the two.

Advantageously, the herbal compositions and methods of the present invention provide an alternative treatment option for subjects suffering from viral infections. In addition, the herbal compositions and methods of the present invention provide an alternative treatment option that exhibits minimal side effects. These and other advantages of the present invention will become readily apparent from the detailed description set forth below.

DETAILED DESCRIPTION OF THE INVENTION

The present invention provides herbal compositions useful for the treatment of viral infections, such as hepatitis, and methods of using these compositions. The herbal compositions of the invention are particularly useful for the treatment of subjects infected with hepatitis B virus and/or hepatitis C virus.

In one embodiment, a primary herbal composition is provided which comprises (a) an extract from the leaves or seed of *Sesbania aegyptiaca* (sesban) and (b) at least one additional herbal extract from either seed of *Nigella sativa*, shoot of *Cichorium intybus* (pumilum), whole plant of *Cymbopogon proximus*, rhizome of *Hemidesmus indicus*, leaves of *Solenostema argel*, rhizome of *Rheum officinale*, or fruit of *Ecballium elaterium*. In an additional embodiment, the composition omits (i.e., does not contain) *Ecballium elaterium* but includes two additional herbal extracts other than *Ecballium elaterium*, with extracts from *Solenostema argel* and *Hemidesmus indicus* being preferred. The above-described herbs exhibit anti-viral activity in addition to other beneficial properties, which facilitates the treatment of viral infections.

The above-described herbs are known in the art and are readily available from a variety of sources. A description of the herbs used in accordance with the present invention is found in "Student's Flore of Egypt" (in English Language), Tackholm, V., published by Cairo University and printed by Cooperative Printing Company, Beirut (1974). Additional descriptions of the herbs are found in the "Illustrated Polyglottic Dictionary of Plant Names," Armenag, K. Bedevian, Cairo Argus and Papazian Press, (1936), the "Encyclopedia of Common Natural Ingredients, Used in Food, Drugs, and Cosmetics," Albert Leung, (1980), and "Medicinal Plants of North Africa," Loutfy Boulos, Reference Publications, Inc. (1983).

*Sesbania aegyptiaca* (sesban), which is a member of the Leguminosae family, is a glabrous shrub that has kidney-shaped yellow flowers with purple-dotted seeds of 3–4 mm in length. The plant is also known in Arabic as Sasaban. The plant is found in North Africa (e.g., Egypt), India, and South America. In addition to its anti-viral properties, extracts of the plant are useful for the treatment of jaundice.

*Nigella sativa*, which is a member of the Ranunculaceace family, is also known in Arabic as Kammun aswad, Sanoudj, Habba souda, Habbet el-barakah, or Kammun el-akhal; in English as Black cumin; and in French as Nigelle, Cumin noir, Toute épice, Quatre épice, or Araignée (Medicinal Plants of North Africa, Loutfy Boulos, Reference Publications, Inc., pp.150–51(1983)). The plant is found in North Africa (e.g., Egypt), India and South America.

*Cichorium intybus* (pumilum), which is a member of the Compositae family, is a plant exhibiting heads in sessile clusters along the stem or solitary on top of thick, swollen peduncles. Involucral scales are slightly hairy, but not glandular. The stem leaves are narrow and the flowers are blue, but rarely white and ligulate. The plant is also known in Arabic as Chicora and Hendepaa. This plant is found in North Africa (e.g., Egypt), Asia, South America and in the United States. In addition to its anti-viral properties, extracts of the plant are useful as hepatoprotectant/tonic, laxative, diuretic and for the treatment of jaundice.

*Cymbopogon proximus* (Andropogon proximus Hochst), which is a member of the Gramineae family, is a stout, densely tufted grass, with narrow leaves. The panicle is reddish, elongated, with short primary branches. The plant is also known in Arabic as Halfa par. The plant is found in North Africa (e.g., Egypt), Asia, and South America. In addition to its anti-viral properties, extracts of the plant are useful as a diuretic.

*Hemidesmus indicus*, which is a member of the Asclepiadaceae family, is a plant with parted roots and golden yellowish in color. The plant grows up to 1–1.5 meters in length with a diameter of 0.25–0.50 cm (Alam, et al., Phytotherapy Research, 10(1):58–61 (1996)). The plant is also known in Arabic as Ushpa. The plant is found in India and in the far-East. In addition to its anti-viral properties, extracts of the plant are useful as a hepatoprotectant/tonic and for the treatment of jaundice.

*Solenostema argel*, which is a member of the Asclepiadaceae family, is an erect perennial plant with white flowers in axillary umbels. The fruit is ovate, smooth, very hard and has a dark purple color. Leaves are elliptical lanceolate with the corolla lobes are erect. The plant is also known in Arabic as Harrgal. The plant is found in North Africa (e.g., Egypt), Israel, the Arabian Gulf countries and India. In addition to its anti-viral properties, extracts of the plant are useful as a laxative.

*Rheum officinale*, which is a member of the Polygonaceae family, is a large and sturdy perennial herb with a stem 2–3 meters in height and large leaves born on thick petals (Yokozbawa, et al., J. Traditional Medicine, 15(4):202–207 (1998)). The plant is also known in Arabic as Rawend. The plant is found in China, India and Southern Siberia. In addition to its anti-viral properties, extracts of the plant are useful as hepatoprotectant/tonic, laxative, diuretic and for the treatment of jaundice.

*Ecballium elaterium*, which is a member of the Curcurbitaceae family, is a plant having yellow flowers and green fruit. The fruit can grow up to 3 cm in length and approximately 15 mm in width. The plant is also called faggous el-hemar in Arabic, the concombre d'ane in French, and the squirting cucumber in English (Medicinal Plants of North Africa, pp. 74–75 (1983)). The plant is found in the lower Mediterranean region (e.g., Libya, Algeria, and Egypt) and in Jordan, Israel and Turkey. In addition to its anti-viral properties, extracts of the plant are useful as a hepatoprotectant/tonic and for treatment of jaundice.

The herbal compositions of the invention can also contain auxiliary herbal extracts to minimize potential side effects associated with the anti-viral herbs and to ameliorate symptoms associated with viral infections, such as hepatitis. Preferably, the herbal compositions contain at least one auxiliary herbal extract from the following herbs: seed of *Foeniculum vulgare*, shoot of *Centaurium erythrae* (spicatum or pulchellum), flowers, leaves or stem of *Cynara cardunculus* var scolymus, root of *Inula helenium* (viscosa) and seed of *Cuminum cyminum*.

*Foeniculum vulgare*, also known as common fennel, is a member of the Umbelliferae family and generally grows up to about 1.5 meters high (Encyclopedia of Common Natural Ingredients, Used in Food, Drugs, and Cosmetics, p.169 (1980)). The dried ripe fruit of this herb is commonly called fennel seed. The plant is also known in Arabic as Shamar. The plant is found in North Africa (Egypt), India and South America. Extracts from this plant can be used in the herbal compositions as a hepatoprotectant/tonic and for treatment of jaundice, to relieve bloating and stomach pain, to stimulate appetite and to act as an anti-inflammatory.

*Centaurium erythrae* (spicatum or pulchellum), which is a member of the Gentianaceae family, is a plant with pedicelled flowers in which the whole plant forms a leafy corymosely cymose inflorescence. The plant is found in North Africa (e.g., Egypt), India, South America and in the United States. Extracts from this plant can be used in the herbal compositions as a hepatoprotectant/tonic, a sedative, an anti-pyretic, and as a digestive aid.

*Cynara cardunculus* var scolymus, also known as the globe artichoke, is a member of the Compositae family. The plant is a large thistle-like perennial herb which grows up to about 1 meter high. The flowers of the plant are purplish and whitish in color. The leaves are large rosettes, pinnatifid, spiny, glabrous above and conescent beneath. The plant is found in North Africa (e.g., Egypt), the Far East, Europe and the United States. Extracts from this plant can be used in the herbal compositions as a hepatoprotectant/tonic, for the treatment of jaundice, and as a digestive aid.

*Inula helenium* (viscosa), which is a member of the Compositae family, is a plant that grows to about 1 to 1.5 meter in height. The leaves are heart shaped with their lower sides being covered by lanceolate and greyish-colored spines. The Flowers are widely rounded and are yellowish in color. Roots are deep brown in color, whitish on the inside and have a characteristic smell. The plant is also known in Arabic as Rasen. This plant is found in Syria, Lebanon, Israel, Europe and the United States. Extracts from this plant can be used in the herbal compositions as a hepatoprotectant/tonic, an anti-inflammatory, an immunostimulant, an appetite stimulator, and as a decongestant.

*Cuminum cyminum*, which is a member of the Umbelliferae family, is a plant with a slender stem and is highly branched above. The plant grows to about 60 cm in height. The seed is oblong-cyclindrical in shape and green in color. The plant is typically found in the Mediterranean region. Extracts from this plant can be used in the herbal compositions as a hepatoprotectant/tonic, a diuretic, an anti-pyretic, an anti-flatulent and as a digestive aid.

In one particular embodiment, a twelve-component herbal composition is provided which comprises extracts from the following herbs:

(a) seed of *Foeniculum vulgare*, with about 12% to 36% by weight being preferred, and about 24% by weight being more preferred;

(b) seed of *Nigella sativa*, with about 11.5% to 34.5% by weight being preferred, and about 23% by weight being more preferred;

(c) shoot of *Centaurium erythrae* (spicatum or pulchellum), with about 5% to 15% by weight being preferred, and about 11% by weight being more preferred;

(d) flowers, leaves or stem of *Cynara cardunculus* var scolymus, with about 3.5% to 10.5% by weight being preferred, and about 7% by weight being more preferred;

(e) root of *Inula helenium* (viscosa), with about 3% to 9% by weight being preferred, and about 6% by weight being more preferred;

(f) leaves of *Solenostema argel*, with about 1% to 6% by weight being preferred, and about 4% by weight being more preferred;

(g) leaves or seed of *Sesbania aegyptiaca* (sesban), with about 0.5% to 8% by weight being preferred, and about 6% by weight being more preferred;

(h) shoot of *Cichorium intybus* (pumilum), with about 3% to 9% by weight being preferred, and about 6% by weight being more preferred;

(i) whole plant of *Cymbopogon proximus*, with about 3.5% to 10.5% by weight being preferred, and about 7% by weight being more preferred;

(j) rhizome of *Hemidesmus indicus*, with about 1% to 3% by weight being preferred, and about 2% by weight being more preferred;

(k) rhizome of *Rheum officinale*, with about 1% to 3% by weight being preferred, and about 2% by weight being more preferred; and (l) seed of *Cuminum cyminum*, with about 1% to 3% by weight being preferred, and about 2% by weight being more preferred.

In another embodiment of the present invention, a five-component herbal composition is provided which comprises extracts from the following herbs:

root of *Inula helenium* (viscosa), with about 3% to 17% by weight being preferred, and about 10% by weight being more preferred;

shoot of *Centaurium erythrae* (spicatum or pulchellum), with about 5% to 27% by weight being preferred, and about 16% by weight being more preferred;

seed of *Nigella sativa*, with about 11.5% to 60% by weight being preferred, and about 60% by weight being more preferred;

leaves or seed of *Sesbania aegyptiaca* (sesban), with about 0.5% to 10% by weight being preferred, and about 8% by weight being more preferred; and rhizome of *Hemidesmus indicus*, with about 1% to 7% by weight being preferred, and about 5% by weight being more preferred.

The present invention also provides a seven-component herbal composition which comprises extracts from the following herbs:

rhizome of *Hemidesmus indicus*, with about 1% to 7% by weight being preferred, and about 4% by weight being more preferred;

flowers, leaves or stem of *Cynara cardunculus* var scolymus, with about 3.5% to 26.5% by weight being preferred, and about 15% by weight being more preferred;

shoot of *Centaurium erythrae* (spicatum or pulchellum), with about 5% to 27% by weight being preferred, and about 17% by weight being more preferred;

seed of *Foeniculum vulgare*, with about 12% to 60% by weight being preferred, and about 39% by weight being more preferred;

leaves of *Solenostema argel*, with about 1% to 7% by weight being preferred, and about 4% by weight being more preferred;

shoot of *Cichorium intybus*, with about 3% to 17% by weight being preferred, and about 10% by weight being more preferred; and leaves or seed of *Sesbania aegyptiaca* (sesban), with about 0.5% to 19.5% by weight being preferred, and about 10% by weight being more preferred.

Another five-component herbal composition is additionally provided which comprises extracts from the following herbs:

seed of *Nigella sativa*, with about 11.5% to 60% by weight being preferred, and about 40% by weight being more preferred;

shoot of *Centaurium erythrae* (spicatum or pulchellum), with about 5% to 27% by weight being preferred, and about 12% by weight being more preferred;

leaves or seed of *Sesbania aegyptiaca* (sesban), with about 0.5% to 19.5% by weight being preferred, and about 10% by weight being more preferred;

seed of *Foeniculum vulgare*, with about 12% to 34% by weight being preferred, and about 23% by weight being more preferred; and whole plant of *Cymbopogon proximus*, with about 3.5% to 26.5% by weight being preferred, and about 15% by weight being more preferred.

In yet another embodiment, the present invention provides a seven-component herbal composition which comprises extracts from the following herbs:

rhizome of *Rheum officinale*, with about 1% to 5% by weight being preferred, and about 3% by weight being more preferred;

seed of *Cuminum cyminum*, with about 1% to 7% by weight being preferred, and about 4% by weight being more preferred;

root of *Inula helenium* (viscosa), with about 3% to 20% by weight being preferred, and about 15% by weight being more preferred;

flowers, leaves or stem of *Cynara cardunculus* var scolymus, with about 3.5% to 46.5% by weight being preferred, and about 25% by weight being more preferred;

seed of *Foeniculum vulgare*, with about 12% to 60% by weight being preferred, and about 42% by weight being more preferred; and leaves or seed of *Sesbania aegyptiaca* (sesban), with about 0.5% to 19.5% by weight being preferred, and about 10% by weight being more preferred.

In the context of the present invention, reference to "weight percent" or "percent by weight" refers to the amounts of the herbal extracts by weight in the composition per 100 grams total weight of the composition. Additional non-herbal extract components (i.e., excipients) in the composition are excluded from the calculation of "weight percent" or "percent by weight."

Extracts of the various herbs are prepared following conventional techniques known in the art. The extracts can be prepared as a powdered extract using a maceration extraction process or as a liquid extract using a solvent extraction process. For example, the herbal compositions may be prepared as herbal extracts as taught in U.S. Pat. No. 5,876,728, or in U.S. Pat. No. 5,874,804. In a preferred embodiment, the multi-component herbal compositions of the invention are prepared as powdered extracts for ease of storage and use.

The herbal compositions are not limited to any one particular dosage form. The compositions of this invention can be prepared in a variety of dosage forms known in the art. However, as will be apparent to those skilled in the art, the particular dosage form used will be dependent on the delivery route. The herbal compositions can also include excipients to alter, taste, bulk, and texture, and can include preservatives to increase shelf-life.

In accordance with the present invention, methods of treating viral infections with the herbal compositions of the invention are also provided. The methods comprise administering to the subject an effective amount of a primary herbal composition which includes:

(a) an extract from the leaves or seed of *Sesbania aegyptiaca* (sesban); and (b) at least one additional herbal extract selected from the group consisting of seed of *Nigella sativa*, shoot of *Cichorium intybus* (pumilum), whole plant of *Cymbopogon proximus*, rhizome of *Hemidesmus indicus*, leaves of *Solenostema argel*, rhizome of *Rheum officinale*, and fruit of *Ecballium elaterium*.

In a more preferred embodiment, the primary herbal composition does not contain *Ecballium elaterium* and includes two additional herbal extracts other than *Ecballium elaterium*. Moreover, when *Ecballium elaterium* is omitted from the primary herbal composition, a secondary herbal composition is also preferably administered to increase the efficacy of treatment. A preferred secondary herbal composition is one containing an extract of the fruit of *Ecballium elaterium*. In the alternative, the secondary herbal composition can also include extracts of other anti-viral herbs known in the art. The primary herbal compositions preferably include the above-described auxiliary herbal extracts which are provided to minimize potential side effects associated with the anti-viral herbs and to ameliorate symptoms associated with the viral infections.

In the context of the invention, "treating" or "treatment" at a minimum refers to inhibiting the progression of the viral infection which can be ascertained qualitatively (e.g., by a reduction in clinical symptoms) or quantitatively (e.g., by a reduction in viral load or other quantifiable criteria.). An "effective" amount is any amount of the herbal composition that inhibits or stops the progression of the viral infection. However, as will be apparent to those skilled in the art, the efficacy of a particular composition on a subject will be affected by a variety of factors including, but not limited to, the method of administration, the body mass and age of the subject, and the stage of the infection (e.g., acute or chronic).

As previously described, the herbal compositions of the present invention are particularly suitable for treating a subject having a viral infection. Viruses to be treated include DNA and RNA virus, with hepatitis B virus (HBV) and the hepatitis C virus (HCV) being particularly preferred. In the treatment of HBV or HCV, inhibition of infection can be qualitatively ascertained by determining the presence or absence of the viral genome by polymerase chain reaction (PCR) and reverse transcriptase polymerase chain reaction (RT-PCR), or by observing a reduction and/or disappearance in clinical symptoms such as jaundice, weakness, right hypochondrial pain, loss of appetite, and other symptoms that are associated with hepatitis infection. Efficacy in treating of HBV or HCV can also be quantitatively ascertained by measuring a reduction in viral load using PCR and RT-PCR or by measuring a reduction (i.e., normalization) in elevated liver enzyme levels (e.g., serum alanine transaminase (ALT) and serum aspartate transaminase (AST)). Alternatively, assays for surface antigens of HBV (e.g., HBsAg) and HCV can also be used.

Subjects to whom the herbal compositions of the invention are administered include any living organism, with mammals such as primates and humans being more preferred. The subject is also preferably in need of treatment (i.e., has a viral infection that requires treatment). Accordingly, in a more preferred embodiment, the subject is infected with HBV, HCV or both.

The herbal compositions are administered to the subject by any technique known in the art. Routes of delivery can include, but are not limited to, oral, intranasal, sublingual, intrapulmonary, rectal, transdermal, parenteral and combinations thereof. Acceptable dosage forms suitable for administration to a subject include, but are not limited to, tablets, capsules, powders, patches, solutions, and suspensions. The compositions of the invention can include a physiologically-acceptable carrier in which the herbal extracts are dispersed. For example, the carrier can be buffered saline if a liquid dosage unit is to be prepared. Procedures for making and administering such dosage forms are well within the abilities of one of ordinary skill in the art.

In one particular embodiment, the subject is administered an effective amount of the compositions of the invention, with the twelve-component herbal composition being preferred as the primary herbal composition. The primary herbal composition is preferably administered orally in powder form in a dosage of 1 to 5 grams, three times per day, with 1 to 3 grams being more preferred. Preferably, a secondary herbal composition is additionally administered to the subject, which preferably contains an extract of the fruit of *Ecballium elaterium* in liquid form. The liquid formulation is preferably administered orally in a dosage of 2 drops, two times per day. In a more preferred embodiment, the liquid drops are administered prior to the powder composition. The combined use of these two herbal compositions have been found to be particularly effective in treating subjects infected with HBV and HCV, as compared to using the compositions alone.

EXAMPLES

The following non-limiting examples illustrate the preparation of the herbal compositions of the present invention and their advantageous use in the treatment of subjects infected with HBV and HCV. Other embodiments within the scope of the claims herein will be apparent to persons of ordinary skill in the art from consideration of the specification or practice of the invention as disclosed herein. The Examples herein are meant to illustrate various aspects of carrying out the invention and are not intended to limit the scope of the invention in any way.

Example I

Preparation of the Herbal Compositions

1. Preparation of the Twelve-Component Herbal Composition (Formulation I)

A twelve-component herbal composition was prepared in powder form using the following dried herbs:

(a) seed of *Foeniculum vulgare*;
(b) seed of *Nigella sativa*;
(c) shoot of *Centaurium erythrae* (spicatum or pulchellum);
(d) flowers and leaves of *Cynara cardunculus* var scolymus;
(e) root of *Inula helenium* (viscosa);
(f) leaves of *Solenostema argel*;
(g) leaves and seed of *Sesbania aegyptiaca* (sesban);
(h) shoot of *Cichorium intybus* (pumilum);
(i) whole plant of *Cymbopogon proximus*;
(j) rhizome of *Hemidesmus indicus*;
(k) rhizome of *Rheum officinale*; and
(l) seed of *Cuminum cyminum*.

All of the herbal components were cleaned and separately ground in a stainless steel grinder having a sieve with 1 mm perforations. Prior to grinding, the seed components were additionally passed through a 60-mesh sieve to remove coarse particles to insure similarity in size. The ground components were then passed through the 60-mesh sieve to separate the larger particles. The larger particles were then reground. The sievings (i.e., powder) for each plant were added to a stainless steel rotating mixing tank in the ratio of 24:23.5:12:7.1:6.1:4.1:6.1:6.1:7.2:2.1:2.1:2.1 to provide the composition with weight percentages of approximately 24%:23%:11%:7%:6%:4%:6%:6%:7%:2%:2%:2% for herbs A:B:C:D:E:F:G:H:I:J:K:L, respectively (Table 2). The herbal components were mixed for at least half an hour. The composition was then reground in the stainless steel grinder to ensure thorough mixing and consistent particle size of less than 60-mesh. The herbal composition was then stored for future use.

TABLE 2

| Herbs | A | B | C | D | E | F | G | H | I | J | K | L |
|---|---|---|---|---|---|---|---|---|---|---|---|---|
| Ratios | 24 | 23.5 | 12 | 7.1 | 6.1 | 4.1 | 6.1 | 6.1 | 7.2 | 2.1 | 2.1 | 2.1 |
| Approx. weight percent (%) | 24 | 23 | 11 | 7 | 6 | 4 | 6 | 6 | 7 | 2 | 2 | 2 |

2. Preparation of Herbal Drops (Formulation II)

Fruit of *Ecballium elaterium* was obtained and washed with clean water. Approximately a half kilogram of fruit and one liter of distilled water were combined in an ordinary house electrical grinder. The fruit was ground for two minutes. The mixture was then poured through a sieve of cotton gauge to separate out the larger fruit particles. The mixture was then filtered using wattman filter paper. The filtrate (i.e., cell sap) was stored in a refrigerator at 10° C. for approximately 5–7 hours to promote the precipitation of microparticles. The filtrate was then filtered using ceramic sterilization candles to remove any microorganisms. The pH was adjusted to approximately 6.8 to 7 using dilute sulphuric acid and sodium bicarbonate. A preservative (thimerosal) was added to the sterilized filtrate to provide a concentration of 0.001 gm/liter. The herbal solution was then placed into 10 cc. dropper bottles under aseptic conditions and stored in the refrigerator at about 4 C. The final concentration of the extract was approximately 0.5 weight % cell sap based on the amount of cell sap dissolved in water (5 gms/1000 ml).

Example II

HCV Blind Study

To determine the efficacy of the herbal compositions of the invention, a three (3) year blind study was conducted with 40 patients infected with the hepatitis C virus. The study involved a nine-month long treatment regimen using the herbal compositions of Example I.

Criteria for entry into the study were as follows: (a) testing serum-positive for HCV antibodies within the last 6 months before entry to the study; (b) testing serum-positive for HCV-RNA by RT-PCR within the last 3 months before entry to the study; (c) exhibiting elevated levels of serum alanine transaminase (ALT) and serum aspartate transaminase (AST) within the last 6 months before entry into the study; and (d) exhibiting ALT levels at least twice the upper normal level within the last 6 months before entry into the study which at no time during this time period dropped to or below the normal level. Patients were excluded from the study if they had another major illness such as major active infections, cancer, or renal failure; evidence of liver disease other than viral hepatitis; or a known history or presence of ascites, hepatomegaly or liver cirrhosis. Patients were also excluded if they were alcoholic or a drug abuser, concurrently used other herbs or folk medicine, concurrently used other anti-viral medication, or demonstrated other unsuitable characteristics including severe allergies or dizziness. Dizziness was considered as a criterion for excluding patients because it occurred sometimes and occasionally after taking the herbal compositions.

RT-PCR of serum was done following conventional techniques using a Sorine kit. RT-PCR was followed by thirty-five (35) cycles of amplification of HCV cDNA. A Triple test (El-Awady, et al., Chem. Clinical Acta, 283(1–2):1–14 (1999)) was also conducted for some patients to assay HCV-RNA in serum and leucocytes (both positive and negative strands). In accordance with this test, negative and positive controls were run with each assay to avoid false negatives and false positives. In addition, as part of the Triple test, subjects were tested for serum viraemia, mature viral genome in peripheral mononuclear cell lysate as well as replicating forms of virus in peripheral leucocytes. This gave an impression of the extrahepatic tissue, in which the absence of replicating forms in extrahepatic tissue after treatment provided a good prognosis of the effectiveness of the herbal compositions.

The serum AST and ALT levels were assayed following known techniques (Bergmeyer and Horder, Clin. Chen. Acta 105147 f. (1980); International Federation of Clinical Chemistry, Scientific Committee, J. Clin. Chem. Biochem., 18:521–534 (1980); Bergmeyer H. U. Principles of Enzymatic Analysis. Verlag Chemic, (1978)). Assay kits manufactured by Stanbio Laboratories, Inc., (USA), Bio. Merieux (France), and Boehringer Mannheim (Germany) were used.

The patients were divided into 4 groups of 10 patients each. The first group (Group A) received placebo drops+ actual herbal mixture (Formulation I). The second group (Group B) received actual herbal drops (Formulation II)+ placebo mixture. The third group (Group C) received placebo drops+placebo mixture. The fourth group (Group D) received actual herbal drops (Formulation II)+actual herbal mixture (Formulation I). The placebo mixture contained (a) 5 wt. % of an extract from leaves of *Majoranum hortensis*, (b) 5 wt. % of an extract from leaves of *Ocimum basilicum*, (c) 15 wt. % of an extract from leaves of *Pisidium guajava*, (d) 25 wt. % of corn silk of *Zea mays*, and (e) 50 wt. % of corn starch of *Zea mays*. The plants were ground and mixed in the appropriate ratios following the procedure in Example I. A 1% glucose solution was used as placebo drops. A summary of the groups are listed in Table 3.

TABLE 3

| Grouping of Patients | Treatment Regimen |
| --- | --- |
| Group A | placebo drops + actual herbal mixture |
| Group B | actual herbal drops + placebo mixture |
| Group C | placebo drops + placebo mixture |
| Group D | actual herbal drops + actual herbal mixture |

All patients were instructed to take the mixture orally 3 times a day, 1–2 grams each time and the drops orally twice a day, 2 drops each time. Patients were instructed to take the drops a quarter of an hour before breakfast and dinner. Drops were instilled orally using traction of the lower lip outwards followed by instillation of the drops in the mucous membrane pocket between the inner side of the lower lip and the outer side of lower gums just below the lower incisors. Upon closure of the mouth, these drops spread sublingually where there is a thin mucous membrane and high vasculature. The drops also spread over the buccal mucous membrane where the active principals in the drops are absorbed. Patients were instructed not to swallow for 5 minutes to increase buccal absorption. Patients were also instructed to take the mixture after swallowing the drops. The mixture was suspended in a liquid, such as a quarter cup of water, or mixed with honey or taken as dry powder, followed by drinking a small amount of water. Patients were instructed to not eat for at least 15 minutes after taking the treatment to allow for better absorption in the stomach. However, patients who demonstrated nausea were allowed to eat within this time frame to reduce the nausea.

During the course of treatment, the daily dose of the mixture varied from 3 to 9 grams. The daily dose of the drops varied from 2 to 6 drops. The dose was varied according to the progress of the disease. Some patients with a high viraemia who responded to therapy by demonstrating a reduction of liver enzymes (ALT/AST) within the first two months of treatment received an increased dosage of up to 3 gms herbal mixture t.d.s. (i.e., 9 gms per day) and 3 drops twice daily (i.e., 6 drops per day). Patients who demonstrated higher enzymatic levels (ALT/AST) within the first 2 months of treatment, or patients who demonstrated dizziness, abdominal gurgling or gaseous distention after taking herbal therapy, were instructed to reduce their dosage to 1 gm of herbal mixture t.d.s. (i.e., 3 gms per day) and 1 drop twice daily (i.e., 2 drops per day). This regimen corrected liver enzymes to within normal range within 2 months and stopped the present symptoms within 3 days.

The health status of each patient was monitored monthly, which included monitoring changes in body weight, blood pressure, eating habits, sleeping habits, strength, pain, and overall appearance. Serum ALT and AST levels were also monitored monthly in addition to other enzyme levels. Following generally accepted practices, normalization of ALT and AST levels was considered to occur when levels fell below twice the normal limits. RT-PCR of patients' serum was additionally performed after 6 months of treatment. The percentage of patients having normal enzyme levels (i.e., less than twice the normal limit) at the beginning of treatment and during the first 4 months of treatment is listed in Table 4. After 4 months, the number of patients that returned for monthly assessment of enzyme levels began to significantly decrease.

TABLE 4

| Grouping of Patients | Initial Percentage with Normal Levels | | Mean Percent Normalization during First 4 Months of Treatment | |
| --- | --- | --- | --- | --- |
| | ALT | AST | ALT | AST |
| Group A | 40.00% | 20.00% | 75.00% | 70.00% |
| Group B | 30.00% | 20.00% | 60.00% | 60.00% |
| Group C | 60.00% | 60.00% | 57.50% | 57.50% |
| Group D | 60.00% | 20.00% | 85.00% | 75.00% |

As can be seen from Table 4, serum ALT and AST levels for the patients in Group D (patients who received actual herbal mixture and actual herbal drops) exhibited the largest increase in normalization. Some patients in Group A (who received the actual mixture and placebo drops) and in Group B (who received placebo mixture and actual drops) also demonstrated an improvement in their serum ALT and AST levels. However, serum ALT and AST levels for Group C did not improve and actually worsened In addition, 5 patients in Group D (50%), 2 patients in Group A (20%), and 3 patients in Group B (30%) tested PCR negative for viral RNA after 6 months of treatment. No patients in Group C became PCR negative. This data is summarized in Table 5 below.

TABLE 5

| | Serum - Negative for HCV-RNA | |
| --- | --- | --- |
| Grouping of Patients | Prior to Treatment | After 6 months |
| Group A | 0% | 20% |
| Group B | 0% | 20% |
| Group C | 0% | 0% |
| Group D | 0% | 50% |

Furthermore, some of the patients in Group D reported an improvement in symptoms associated with hepatitis such as:
1. Increase in strength sufficient to allow patient work efficiently;
2. Disappearance of right hypochondrial pain and so the patient can sleep on his right side;
3. An improvement of prothrombine synthesis and a corresponding decrease in bleeding;
4. Healing of skin lesions, disappearance of tenderness of skin and soft tissues, and clearance of skin pigmentations in hepatic patients;
5. Improvement of appetite and digestion;
6. Loss of constipation and correction of bowel habits;
7. Disappearance of an earthy look of the face;
8. Decrease attacks of cholecystitis; and
9. Weight gain.

Some patients in Groups A and B also exhibited similar improvements, but to a lesser extent. Patients in Group C exhibited only improvements in appetite, digestion and loss of constipation.

Example III

HBV Blind Study

A five (5) year blind study was conducted with patients infected with HBV to ascertain the efficacy of the herbal mixture and herbal drops of Example 1. The study was conducted on 22 patients who were chronic carriers of HBV. Criteria for entry into the study were as follows:(a) testing serum-positive for HBs antigen within the last 6 months prior to the study; (b) testing serum-positive for HBV-DNA by PCR within the last 3 months before entry to the study; (c) exhibiting elevated levels of serum alanine transaminase (ALT) and serum aspartate transaminase (AST) within the last 6 months before entry into the study; and (d) exhibiting ALT levels at least twice the upper normal level within the last 6 months before entry into the study which at no time during this time period dropped to or below the normal level.

The patients were divided into four groups, Groups A–C had 5 patients each, while Group D had 7 patients. The groups were treated as follows: Group A received placebo herbal drops+actual herbal mixture (Formulation I); Group B received actual herbal drops (Formulation II)+placebo herbal mixture; Group C received placebo herbal drops+ placebo herbal mixture; and Group D received actual herbal drops (Formulation II)+actual herbal mixture (Formulation I). A summary of Groups A–D is listed in Table 6.

TABLE 6

| Grouping of Patients | Treatment Regimen |
| --- | --- |
| Group A | placebo drops + actual herbal mixture |
| Group B | actual herbal drops + placebo mixture |
| Group C | placebo drops + placebo mixture |
| Group D | actual herbal drops + actual herbal mixture |

All patients were initially instructed to take the mixture orally three times a day, 1–2 grams each time and to take the oral drops twice a day, 2 drops each time. The dose was varied according to the progress of the disease, where mixture varied from 3 to 9 grams and drops from 2 to 6 per day.

Serum ALT and AST levels and health status were monitored monthly as in Example II. Qualitative PCR of patients' serum for HBV-DNA was conducted after 6 months of treatment.

Of the four groups, Group D (which received the actual herbal mixture and drops) exhibited the best results where 4 out of 7 patients (57.14%) tested serum-negative for HBV-DNA and exhibited normalized enzyme levels. An improvement in clinical symptoms was also observed for all 7 patients within three months from the start of treatment. In Group D liver enzymes including ALT and AST returned to normal levels in 90% of the patients after −3 months of treatment which increased to 100% after 4 months of treatment. Patients in Groups A and B only demonstrated partial clinical improvement and only 40% tested serum-negative for HBV-DNA. The patients in Group C (which received the placebo mixture and placebo drops) did not exhibit any improvement as demonstrated by liver enzymes levels, PCR and clinical symptoms. Summaries of the PCR results, and the normalization of enzyme levels during the first 4 months of treatment, are listed in Tables 7 and 8, respectively.

TABLE 7

| | Serum - Negative for HBV-DNA | |
| --- | --- | --- |
| Grouping of Patients | Prior to Treatment | After 6 Months |
| Group A | 0% | 40% |
| Group B | 0% | 40% |
| Group C | 0% | 0% |
| Group D | 0% | 57% |

TABLE 8

| Grouping of Patients | Initial Percentage with Normal Levels | | Mean Percent Normalization during First 4 Months of Treatment | |
| --- | --- | --- | --- | --- |
| | ALT | AST | ALT | AST |
| Group A | 60.00% | 40.00% | 60.00% | 60.00% |
| Group B | 60.00% | 80.00% | 100.00% | 100.00% |
| Group C | 60.00% | 40.00% | 80.00% | 100.00% |
| Group D | 42.86% | 71.43% | 100.00% | 100.00% |

Example IV

HBV/HCV Blind Study

A study was conducted with patients infected with both HBV and HCV to ascertain the efficacy of the herbal mixture and herbal drops of Example I. The study was conducted with 8 patients. Criteria for entry into the study followed the entry criteria for HCV and HBV studies described in Examples II and III, respectively. Patients were instructed to take the herbal mixture and drops following the treatment regimen described in Examples II and III. The patients were monitored as described in Examples II and III. Summaries of the PCR results, and the normalization of enzyme levels during the first 3 months of treatment, are listed in Tables 9 and 10, respectively.

TABLE 9

| Serum - Negative for HCV-RNA | | Serum - Negative for HBV-DNA | |
| --- | --- | --- | --- |
| Prior to Treatment | After 6 Months | Prior to Treatment | After 6 Months |
| 0% | 37.5% | 0% | 50% |

TABLE 10

| Initial Percentage with Normal Levels | | Mean Percent Normalization during First 3 months of Treatment | |
| --- | --- | --- | --- |
| ALT | AST | ALT | AST |
| 12.5% | 37.5% | 75.0% | 85.0% |

As can be seen from Tables 9 and 10, the herbal compositions of the invention are effective in treating patients infected with both hepatitis B and hepatitis C. After six months of treatment, 37.5% of the patients were serum-negative for HCV-RNA while 50% percent of the patients were serum-negative for HBV-DNA. Likewise, the patients exhibited a significant increase in normalization of ALT and AST levels as measured during the first three months of treatment.

Various references cited throughout this application are incorporated herein in their entirety by reference.

We claim:

1. A method for treating a viral infection, comprising administering to a subject in need thereof, an effective amount of a primary herbal composition comprising:
    (a) an extract from the leaves or seed of *Sesbania aegyptiaca* (sesban) in an amount of about 6% by weight;
    (b) an extract of seed of *Nigella sativa* in an amount of about 23% by weight, an extract of the shoot of *Cichorium intybus* (pumilum) in an amount of about 6% by weight, an extract of *Cymbopogon proximus* in an amount of about 7% by weight, an extract of the rhizome of *Hemidesmus indicus* in an amount of about 2% by weight, an extract of the leaves of *Solenostema argel* in an amount of about 4% by weight and an extract of the rhizome of *Rheum officinale* in an amount of about 2% by weight and an extract of the fruit of *Ecballium elaterium*; and
    (c) an extract of the seed of *Foeniculum vulgare* in an amount of about 24% by weight, an extract of the shoot of *Centaurium erythrae* (spicatum or pulchellum) in an amount of about 11% by weight, an extract of the flowers, leaves or stem of *Cynara cardunculus* var *scolymus* in an amount of about 7% by weight, an extract of the root of *Inula helenium* (viscosa) in an amount of about 6% by weight and an extract of the seed of *Cuminum cyminum* in an amount of about 2% by weight, wherein the viral infection is selected from the group consisting of hepatitis B virus infection, hepatitis C virus infection, and a combined hepatitis B virus and hepatitis C virus infection.

2. The method according to claim 1, wherein the subject is a mammal.

3. The method according to claim 2, wherein the mammal is a human.

* * * * *